United States Patent [19]

Rhynard

[11] Patent Number: 4,513,606
[45] Date of Patent: Apr. 30, 1985

[54] SURFACTANT MONITOR FOR AVIATION FUEL FILTER/SEPARATORS

[75] Inventor: Donald L. Rhynard, Yardley, Pa.

[73] Assignee: Mobil Oil Corporation, New York, N.Y.

[21] Appl. No.: 407,201

[22] Filed: Aug. 11, 1982

[51] Int. Cl.³ ............................................. G01N 15/00
[52] U.S. Cl. ..................................... 73/61 R; 210/85
[58] Field of Search ........................... 73/61 R, 61.1 R; 210/86, 96.2, 295, 85, DIG. 5

[56] References Cited

PUBLICATIONS

*Analysis and Control of Contamination in Aviation Fuels,* Millipore Corp. publication AG-1, published 1966.

*Primary Examiner*—Howard A. Birmiel
*Assistant Examiner*—Joseph W. Roskos
*Attorney, Agent, or Firm*—A. J. McKillop; Michael G. Gilman; Frank J. Kowalski

[57] ABSTRACT

A method and apparatus is provided for indicating the effectiveness of aviation fuel filters and separators wherein a small Teflon monitor is installed in conjunction with paper separator elements and is periodically removed to test the surfactant level within the aviation fuel filters and separators.

2 Claims, 3 Drawing Figures

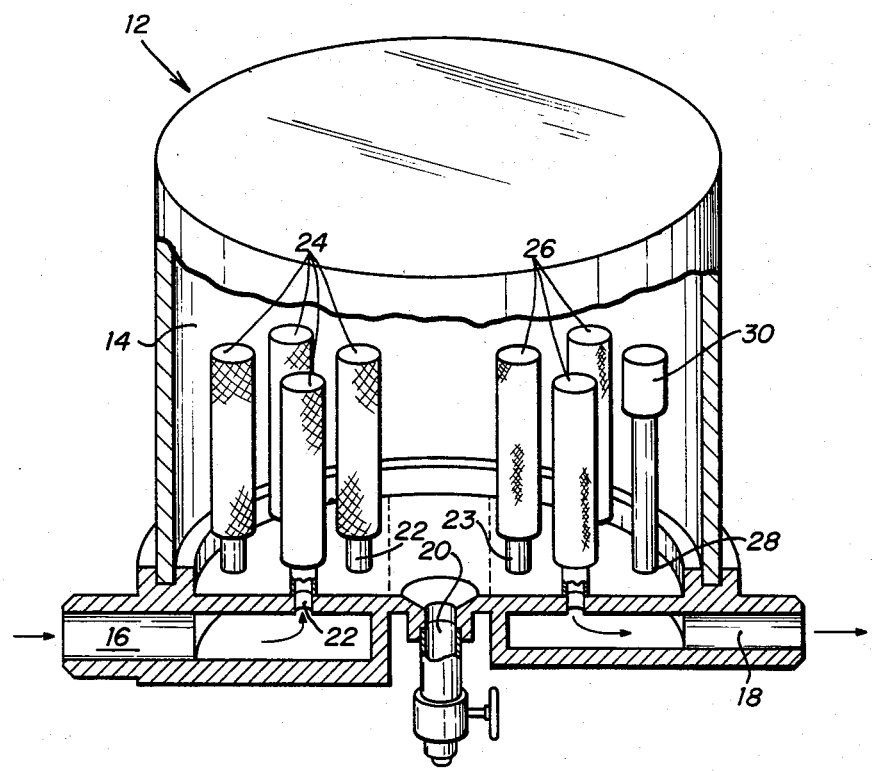
FIG. 1
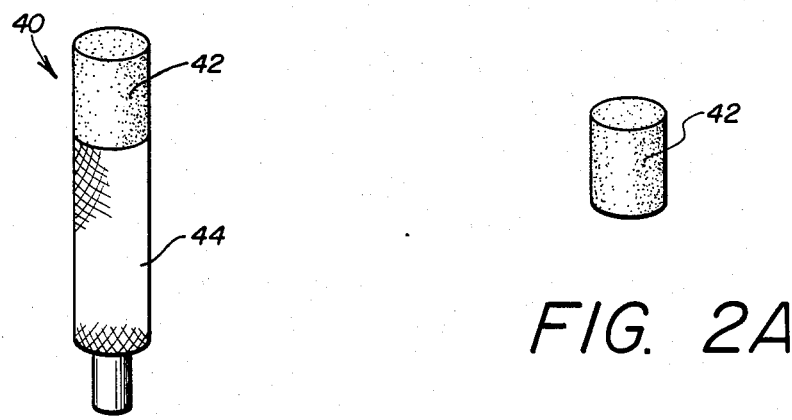
FIG. 2
FIG. 2A

SURFACTANT MONITOR FOR AVIATION FUEL FILTER/SEPARATORS

BACKGROUND OF THE INVENTION

In present oil distribution and marketing, a major problem is moisture in the hydrocarbon fuel supplied to the consumer. There exist many methods for removing moisture from the fuel prior to dispensing. One widely used method is to flow the fuel through a filter/separator.

A filter/separator is normally composed of two stages. The first stage, called the coalescer, removes dirt and coalesces finely dispersed moisture into discrete water droplets. Most of the water droplets fall by gravity to a sump and are drained. The second stage, called the separator, removes finer water droplets which are comingled with the fuel. In the first stage, disposable coalescer elements are used. Either paper elements or "Teflon" elements may be used in the second stage as separator elements.

The stages will remove dirt and water from fuel, such as that used in aviation, effectively as long as the elements are structurally sound and have not been contaminated with surfactants. The elements in both stages are normally changed on an elapsed time basis provided that a gravimetric millipore test on the effluent fuel remains satisfactory and the elements maintain a predetermined flow rate. Once the elements become plugged with particulate matter the pressure drop across the filter/separator will change indicating that the elements are no longer effective and must be replaced, in addition to changing the elements on an elapsed time basis.

If the coalescer elements and separator elements become contaminated with surfactants, dispersed water will not be removed plus fine particulate matter may not be removed. Of the two types of separator elements described, paper separator elements are preferred since they have superior filtration ability and are less susceptible to damage during installation. In addition, paper separator elements have a lower initial cost as compared to "Teflon" separator elements. However, there is presently no convenient test for surfactant contamination of either the coalescers or the paper separator elements.

SUMMARY OF THE INVENTION

An improved filter/separator for use in fuel distribution systems is disclosed wherein a monitor, preferably made of "Teflon" mounted within a filter/separator unit along with coalescers and paper separator elements. The monitor is exposed to a higher surfactant level and is contaminated prior to the coalescer and paper separator. The monitor is tested periodically as an indicator of surfactant contamination.

BRIEF DESCRIPTION OF THE DRAWINGS

FIG. 1 is a plan view of a filter/separator unit.
FIG. 2 is a plan view of a surfactant monitor.
FIG. 2A is a plan view of a portion of FIG. 2.

DESCRIPTION OF THE PREFERRED EMBODIMENT

Referring to FIG. 1, a filter/separator unit 12 is illustrated as having a housing unit 14 and inlet conduit 16 and outlet conduit 18 and a drain opening 20. Located within housing 14 are support posts 22 upon which are mounted coalescers 24 and support posts 23 upon which are mounted paper/separators 26. Mounted upon support post 28 is a "Teflon" screen monitor 30.

In operation, a fuel, such as aviation fuel, flows through inlet 16 through support posts 22 into housing 14 where it initially contacts coalescers 24. Coalescers 24 remove larger dirt particles and coalesces finely dispersed water into discrete water droplets. The water droplets which have a density higher than that of the fuel travel down coalescers 24 by gravity to a sump and are exhausted through drain 20. The fuel travels through separators 26 through support posts 23 to outlet 18. After the fuel contacts coalescers 24 and before it flows through outlet 18 it contacts paper/separators 26 which has a small mesh and removes the fine water droplets which are comingled with the fuel. These finer water droplets, which again have a density greater than that of the fuel, similarly travel down paper separators 26 to a sump and are exhausted through drain 20.

Mounted on support post 28 is a monitor 30 which is exposed to the fuel flow to the same extent that paper filters 26 are. However, monitor 30 is constructed of a fluorocarbon polymer such as "Teflon" while separators 26 are constructed of paper. Fluorocarbon polymers have a higher unit of area porosity than the paper and therefore offer less restriction to fuel flow. Therefore, monitor 30 will have a greater propensity to surfactant contamination and fail to remove moisture from the fuel prior to the failure of separators 26. Furthermore, there is presently no convenient test for surfactant contamination in either the coalescers nor the paper/separator elements. As such, it is presently more economical to merely replace all of paper/separators 26 and coalescers 24 on an elapsed time basis based upon their average life. Monitor 30 is constructed of a fluorocarbon polymer which can be tested for surfactant contamination without destruction. By performing yearly inspections and testing monitor 30 for surfactant contamination, the surfactant contamination of paper/separators 26 and coalescers 24 can be interpolated.

Referring now to FIGS. 2 and 2A, an embodiment of the present invention is illustrated as monitor/separator element 40. Element 40 is generally cylindrically shaped, a length approximately equal to its diameter. In FIG. 2A, a single monitor is illustrated while in FIG. 2, monitor/separator element 40 is composed of two parts. A first part, 42 which is constructed of a fluorocarbon polymer, may be identical to that illustrated in FIG. 2A, such as "Teflon". A second part, 44 which is constructed of paper similar to separators 26 (See FIG. 1). Under standard fuel dispensing conditions, part 42 will be exposed to fuel flow to the same extent as part 44. Part 42 and part 44 may be joined together by any method presently used in the art or may be stacked one on top of the other.

Fluorocarbon polymer part 42 is significantly smaller than paper/filter part 44 since only a small portion of a separator element need be tested to determine surfactant contamination.

The foregoing preferred embodiment and alternate embodiment illustrate a method and apparatus for an accurate determination of the surfactant contamination in filter elements contained within a filter/separator unit. By providing an element which can be tested for surfactant contamination, the method of replacing all filters and coalescers from a filter/separator unit on an elapsed time basis may be eliminated. Periodic checks and testing of the monitor provides an accurate determination of whether surfactants have contaminated the unit and fuel with an unacceptable moisture content being delivered.

While the present invention has been illustrated by way of preferred embodiment, and an alternate embodiment, it is to be understood that it is not to be limited thereto but only by the scope of the following claims.

What is claimed is:

1. In a filter/separator unit having two stages for separating moisture and filtering particulate matter the improvement comprising:
a replaceable cylindrical element for monitoring cumulative saturation of separating elements used to separate moisture from aviation fuel, constructed of a material readily testable for surfactant contamination, said cylindrical element adapted to be replaced in the unit whenever said separating elements have a moisture content below a predetermined level.

2. A surfactant monitor comprising:
a generally cylindrical shaped element having a length approximately equal to its diameter constructed of a material testable for cumulative surfactant contamination, said element adapted for continued use whenever said surfactant contamination is below a predetermined level.

* * * * *